(12) United States Patent
Hoarau

(10) Patent No.: US 8,175,671 B2
(45) Date of Patent: May 8, 2012

(54) MEDICAL SENSOR FOR REDUCING SIGNAL ARTIFACTS AND TECHNIQUE FOR USING THE SAME

(75) Inventor: Carine Hoarau, Lafayette, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1467 days.

(21) Appl. No.: 11/525,635

(22) Filed: Sep. 22, 2006

(65) Prior Publication Data

US 2008/0076994 A1 Mar. 27, 2008

(51) Int. Cl.
*A61B 5/1455* (2006.01)
(52) U.S. Cl. .................... 600/344; 600/310; 600/323
(58) Field of Classification Search .............. 600/309, 600/310, 322, 323, 340, 344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,321,930 A | 3/1982 | Jobsis et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,510,938 A | 4/1985 | Jobsis et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |

(Continued)

FOREIGN PATENT DOCUMENTS

AU 732799 5/2001

(Continued)

OTHER PUBLICATIONS

U.S. Appl. No. 11/507,814, filed Aug. 22, 2006, Baker et al.

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

A sensor may be adapted to reduce motion artifacts by mitigating the effects of the tissue moving within the sensor. A sensor is provided with an elastomeric sensor body adapted to accommodate patient motion. Further, a sensor is provided in which the sensor cable is arranged to mitigate its pressure on a patient's tissue.

20 Claims, 8 Drawing Sheets

U.S. PATENT DOCUMENTS

| | | | |
|---|---|---|---|
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,783,815 A | 11/1988 | Buttner | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A * | 5/1989 | Tan et al. | 600/344 |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,041,187 A | 8/1991 | Hink et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,086,229 A | 2/1992 | Rosenthal et al. | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| D326,715 S | 6/1992 | Schmidt | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,207 A | 6/1993 | Rosenthal | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,267,566 A | 12/1993 | Choucair et al. | |
| 5,273,036 A | 12/1993 | Kronberg et al. | |
| 5,275,159 A | 1/1994 | Griebel | |
| 5,278,627 A | 1/1994 | Aoyagi et al. | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,348,005 A | 9/1994 | Merrick et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |

| Patent No. | Date | Inventor(s) | Patent No. | Date | Inventor(s) |
|---|---|---|---|---|---|
| 5,398,680 A | 3/1995 | Polson et al. | 5,662,106 A | 9/1997 | Swedlow et al. |
| 5,402,777 A | 4/1995 | Warring et al. | 5,664,270 A | 9/1997 | Bell et al. |
| 5,402,779 A | 4/1995 | Chen et al. | 5,666,952 A | 9/1997 | Fuse et al. |
| 5,411,023 A | 5/1995 | Morris, Sr. et al. | 5,671,529 A | 9/1997 | Nelson |
| 5,411,024 A | 5/1995 | Thomas et al. | 5,673,692 A | 10/1997 | Schulze et al. |
| 5,413,099 A | 5/1995 | Schmidt et al. | 5,673,693 A | 10/1997 | Solenberger |
| 5,413,100 A | 5/1995 | Barthelemy et al. | 5,676,139 A | 10/1997 | Goldberger et al. |
| 5,413,101 A | 5/1995 | Sugiura | 5,676,141 A | 10/1997 | Hollub |
| 5,413,102 A | 5/1995 | Schmidt et al. | 5,678,544 A | 10/1997 | DeLonzor et al. |
| 5,417,207 A | 5/1995 | Young et al. | 5,680,857 A | 10/1997 | Pelikan et al. |
| 5,421,329 A | 6/1995 | Casciani et al. | 5,685,299 A | 11/1997 | Diab et al. |
| 5,425,360 A | 6/1995 | Nelson | 5,685,301 A | 11/1997 | Klomhaus |
| 5,425,362 A | 6/1995 | Siker et al. | 5,687,719 A | 11/1997 | Sato et al. |
| 5,427,093 A | 6/1995 | Ogawa et al. | 5,687,722 A | 11/1997 | Tien et al. |
| 5,429,128 A | 7/1995 | Cadell et al. | 5,692,503 A | 12/1997 | Kuenstner |
| 5,429,129 A | 7/1995 | Lovejoy et al. | 5,692,505 A | 12/1997 | Fouts |
| 5,431,159 A | 7/1995 | Baker et al. | 5,709,205 A | 1/1998 | Bukta |
| 5,431,170 A | 7/1995 | Mathews | 5,713,355 A | 2/1998 | Richardson et al. |
| 5,437,275 A | 8/1995 | Amundsen et al. | 5,724,967 A | 3/1998 | Venkatachalam |
| 5,438,986 A | 8/1995 | Disch et al. | 5,727,547 A | 3/1998 | Levinson et al. |
| 5,448,991 A | 9/1995 | Polson et al. | 5,730,124 A | 3/1998 | Yamauchi |
| 5,452,717 A | 9/1995 | Branigan et al. | 5,731,582 A | 3/1998 | West |
| 5,465,714 A | 11/1995 | Scheuing | D393,830 S | 4/1998 | Tobler et al. |
| 5,469,845 A | 11/1995 | DeLonzor et al. | 5,743,260 A | 4/1998 | Chung et al. |
| RE35,122 E | 12/1995 | Corenman et al. | 5,743,262 A | 4/1998 | Lepper, Jr. et al. |
| 5,482,034 A | 1/1996 | Lewis et al. | 5,743,263 A | 4/1998 | Baker, Jr. |
| 5,482,036 A | 1/1996 | Diab et al. | 5,746,206 A | 5/1998 | Mannheimer |
| 5,485,847 A | 1/1996 | Baker, Jr. | 5,746,697 A | 5/1998 | Swedlow et al. |
| 5,490,505 A | 2/1996 | Diab et al. | 5,752,914 A | 5/1998 | DeLonzor et al. |
| 5,490,523 A | 2/1996 | Isaacson et al. | 5,755,226 A | 5/1998 | Carim et al. |
| 5,491,299 A | 2/1996 | Naylor et al. | 5,758,644 A | 6/1998 | Diab et al. |
| 5,494,032 A | 2/1996 | Robinson et al. | 5,760,910 A | 6/1998 | Lepper, Jr. et al. |
| 5,494,043 A | 2/1996 | O'Sullivan et al. | 5,766,125 A | 6/1998 | Aoyagi et al. |
| 5,497,771 A | 3/1996 | Rosenheimer | 5,766,127 A | 6/1998 | Pologe et al. |
| 5,499,627 A | 3/1996 | Steuer et al. | 5,769,785 A | 6/1998 | Diab et al. |
| 5,503,148 A | 4/1996 | Pologe et al. | 5,772,587 A | 6/1998 | Gratton et al. |
| 5,505,199 A | 4/1996 | Kim | 5,774,213 A | 6/1998 | Trebino et al. |
| 5,507,286 A | 4/1996 | Solenberger | 5,776,058 A | 7/1998 | Levinson et al. |
| 5,511,546 A | 4/1996 | Hon | 5,776,059 A | 7/1998 | Kaestle |
| 5,517,988 A | 5/1996 | Gerhard | 5,779,630 A | 7/1998 | Fein et al. |
| 5,520,177 A | 5/1996 | Ogawa et al. | 5,779,631 A | 7/1998 | Chance |
| 5,521,851 A | 5/1996 | Wei et al. | 5,782,237 A | 7/1998 | Casciani et al. |
| 5,522,388 A | 6/1996 | Ishikawa et al. | 5,782,756 A | 7/1998 | Mannheimer |
| 5,524,617 A | 6/1996 | Mannheimer | 5,782,757 A | 7/1998 | Diab et al. |
| 5,529,064 A | 6/1996 | Rall et al. | 5,782,758 A | 7/1998 | Ausec et al. |
| 5,533,507 A | 7/1996 | Potratz et al. | 5,786,592 A | 7/1998 | Hök |
| 5,551,423 A | 9/1996 | Sugiura | 5,788,634 A | 8/1998 | Suda et al. |
| 5,551,424 A | 9/1996 | Morrison et al. | 5,790,729 A | 8/1998 | Pologe et al. |
| 5,553,614 A | 9/1996 | Chance | 5,792,052 A | 8/1998 | Isaacson et al. |
| 5,553,615 A | 9/1996 | Carim et al. | 5,795,292 A | 8/1998 | Lewis et al. |
| 5,555,882 A | 9/1996 | Richardson et al. | 5,797,841 A | 8/1998 | DeLonzor et al. |
| 5,558,096 A | 9/1996 | Palatnik | 5,800,348 A | 9/1998 | Kaestle |
| 5,560,355 A | 10/1996 | Merchant et al. | 5,800,349 A | 9/1998 | Isaacson et al. |
| 5,564,417 A | 10/1996 | Chance | 5,803,910 A | 9/1998 | Potratz |
| 5,575,284 A | 11/1996 | Athan et al. | 5,807,246 A | 9/1998 | Sakaguchi et al. |
| 5,575,285 A | 11/1996 | Takanashi et al. | 5,807,247 A | 9/1998 | Merchant et al. |
| 5,577,500 A | 11/1996 | Potratz | 5,807,248 A | 9/1998 | Mills |
| 5,582,169 A | 12/1996 | Oda et al. | 5,810,723 A | 9/1998 | Aldrich |
| 5,584,296 A | 12/1996 | Cui et al. | 5,810,724 A | 9/1998 | Gronvall |
| 5,588,425 A | 12/1996 | Sackner et al. | 5,813,980 A | 9/1998 | Levinson et al. |
| 5,588,427 A | 12/1996 | Tien | 5,817,008 A | 10/1998 | Rafert et al. |
| 5,590,652 A | 1/1997 | Inai | 5,817,009 A | 10/1998 | Rosenheimer et al. |
| 5,595,176 A | 1/1997 | Yamaura | 5,817,010 A | 10/1998 | Hibl |
| 5,596,986 A | 1/1997 | Goldfarb | 5,818,985 A | 10/1998 | Merchant et al. |
| 5,611,337 A | 3/1997 | Bukta | 5,820,550 A | 10/1998 | Polson et al. |
| 5,617,852 A | 4/1997 | MacGregor | 5,823,950 A | 10/1998 | Diab et al. |
| 5,619,992 A | 4/1997 | Guthrie et al. | 5,823,952 A | 10/1998 | Levinson et al. |
| 5,626,140 A | 5/1997 | Feldman et al. | 5,827,179 A | 10/1998 | Lichter et al. |
| 5,630,413 A | 5/1997 | Thomas et al. | 5,827,182 A | 10/1998 | Raley et al. |
| 5,632,272 A | 5/1997 | Diab et al. | 5,829,439 A | 11/1998 | Yokosawa et al. |
| 5,632,273 A | 5/1997 | Suzuki | 5,830,135 A | 11/1998 | Bosque et al. |
| 5,634,459 A | 6/1997 | Gardosi | 5,830,136 A | 11/1998 | DeLonzor et al. |
| 5,638,593 A | 6/1997 | Gerhardt et al. | 5,830,137 A | 11/1998 | Scharf |
| 5,638,816 A | 6/1997 | Kiani-Azarbayjany et al. | 5,839,439 A | 11/1998 | Nierlich et al. |
| 5,638,818 A | 6/1997 | Diab et al. | RE36,000 E | 12/1998 | Swedlow et al. |
| 5,645,060 A | 7/1997 | Yorkey et al. | 5,842,979 A | 12/1998 | Jarman et al. |
| 5,645,440 A | 7/1997 | Tobler et al. | 5,842,981 A | 12/1998 | Larsen et al. |
| 5,660,567 A | 8/1997 | Nierlich et al. | 5,842,982 A | 12/1998 | Mannheimer |
| 5,662,105 A | 9/1997 | Tien | 5,846,190 A | 12/1998 | Woehrle |

| Patent | Date | Inventor |
|---|---|---|
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil |
| 6,061,584 A * | 5/2000 | Lovejoy et al. ............... 600/344 |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllerman et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,715 A | 12/2000 | Larsen et al. |
| 6,165,005 A | 12/2000 | Mills et al. |
| 6,171,258 B1 | 1/2001 | Karakasoglu et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grinblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,278,889 B1 * | 8/2001 | Robinson ..................... 600/323 |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |

| | | |
|---|---|---|
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,618,614 B1 | 9/2003 | Chance |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B2 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |

| | | |
|---|---|---|
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,831,741 B1 | 12/2004 | De Kruif et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 * | 4/2006 | Ito et al. |
| 7,027,849 B2 | 4/2006 | Al-Ali |
| 7,027,850 B2 * | 4/2006 | Wasserman |
| 7,039,449 B2 * | 5/2006 | Al-Ali |
| 7,043,289 B2 * | 5/2006 | Fine et al. |
| 7,047,055 B2 | 5/2006 | Boas et al. |
| 7,060,035 B2 | 6/2006 | Wasserman |
| 7,062,307 B2 * | 6/2006 | Norris et al. |
| 7,067,893 B2 * | 6/2006 | Mills et al. |
| 7,072,701 B2 * | 7/2006 | Chen et al. |
| 7,072,702 B2 * | 7/2006 | Edgar, Jr. et al. |
| 7,079,880 B2 * | 7/2006 | Stetson |
| 7,085,597 B2 * | 8/2006 | Fein et al. |
| 7,096,052 B2 * | 8/2006 | Mason et al. |
| 7,096,054 B2 | 8/2006 | Abdul-Hafiz et al. |
| 7,107,088 B2 * | 9/2006 | Aceti |
| 7,113,815 B2 * | 9/2006 | O'Neil et al. |
| 7,117,590 B2 | 10/2006 | Koenig et al. |
| 7,123,950 B2 * | 10/2006 | Mannheimer |
| 7,127,278 B2 * | 10/2006 | Melker et al. |
| 7,130,671 B2 * | 10/2006 | Baker, Jr. et al. |
| 7,132,641 B2 * | 11/2006 | Schulz et al. |
| 7,133,711 B2 * | 11/2006 | Chernoguz et al. |
| 7,139,559 B2 * | 11/2006 | Kenagy et al. |
| 7,142,901 B2 * | 11/2006 | Kiani et al. |
| 7,161,484 B2 | 1/2007 | Tsoukalis |
| 7,162,288 B2 * | 1/2007 | Nordstrom et al. |
| 7,164,938 B2 | 1/2007 | Geddes et al. |
| 7,190,987 B2 * | 3/2007 | Lindekugel et al. |
| 7,198,778 B2 * | 4/2007 | Achilefu et al. |
| 7,215,984 B2 * | 5/2007 | Diab et al. |
| 7,225,006 B2 | 5/2007 | Al-Ali et al. |
| 7,228,161 B2 | 6/2007 | Chin |
| 7,236,811 B2 * | 6/2007 | Schmitt |
| 7,248,910 B2 * | 7/2007 | Li et al. |
| 7,251,518 B2 | 7/2007 | Herrmann |
| 7,254,433 B2 * | 8/2007 | Diab et al. |
| 7,254,434 B2 | 8/2007 | Schulz et al. |
| 7,260,425 B2 | 8/2007 | Chin et al. |
| 7,280,858 B2 | 10/2007 | Al-Ali et al. |
| 7,289,837 B2 | 10/2007 | Mannheimer et al. |
| 7,295,866 B2 | 11/2007 | Al-Ali |
| 7,297,119 B2 | 11/2007 | Westbrook et al. |
| 7,305,262 B2 | 12/2007 | Brodnick et al. |
| 7,313,425 B2 | 12/2007 | Finarov et al. |
| 7,315,753 B2 | 1/2008 | Baker, Jr. et al. |
| 7,330,746 B2 | 2/2008 | Demuth et al. |
| 7,341,560 B2 | 3/2008 | Henderson et al. |
| 7,412,272 B2 | 8/2008 | Medina et al. |
| 7,433,726 B2 | 10/2008 | Perkins |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0103423 A1 | 8/2002 | Chin et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |

| | | | |
|---|---|---|---|
| 2003/0100840 A1 | 5/2003 | Sugiura et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0127779 A1 | 7/2004 | Steuer et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2005/0004479 A1 | 1/2005 | Townsend et al. |
| 2005/0014999 A1 | 1/2005 | Rahe-Meyer |
| 2005/0017864 A1 | 1/2005 | Tsoukalis |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0059869 A1 | 3/2005 | Scharf et al. |
| 2005/0070773 A1 | 3/2005 | Chin |
| 2005/0070775 A1 | 3/2005 | Chin et al. |
| 2005/0070776 A1 | 3/2005 | Mannheimer et al. |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0197548 A1 | 9/2005 | Dietiker |
| 2005/0222502 A1 | 10/2005 | Cooper |
| 2005/0228248 A1 | 10/2005 | Dietiker |
| 2005/0228299 A1 | 10/2005 | Banet et al. |
| 2005/0256386 A1 | 11/2005 | Chan |
| 2005/0272986 A1 | 12/2005 | Smith |
| 2005/0277819 A1 | 12/2005 | Kiani et al. |
| 2005/0283082 A1 | 12/2005 | Geddes et al. |
| 2006/0020179 A1 | 1/2006 | Anderson |
| 2006/0030764 A1 | 2/2006 | Porges |
| 2006/0058594 A1 | 3/2006 | Ishizuka et al. |
| 2006/0058595 A1 | 3/2006 | Herrmann |
| 2006/0063995 A1 | 3/2006 | Yodh et al. |
| 2006/0064024 A1 | 3/2006 | Schnall |
| 2006/0069319 A1 | 3/2006 | Elhag et al. |
| 2006/0074280 A1 | 4/2006 | Martis |
| 2006/0079794 A1 | 4/2006 | Liu et al. |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0149149 A1 | 7/2006 | Schmid |
| 2006/0155198 A1 | 7/2006 | Schmid |
| 2006/0173257 A1 | 8/2006 | Nagai |
| 2006/0224053 A1 | 10/2006 | Black et al. |
| 2006/0253007 A1 | 11/2006 | Cheng et al. |
| 2006/0253010 A1 | 11/2006 | Brady et al. |
| 2006/0264726 A1 | 11/2006 | Mannheimer et al. |
| 2006/0264727 A1 | 11/2006 | Mannheimer et al. |
| 2006/0281984 A1 | 12/2006 | Mannheimer et al. |
| 2007/0027375 A1 | 2/2007 | Melker et al. |
| 2007/0027376 A1 | 2/2007 | Todokoro et al. |
| 2007/0032707 A1 | 2/2007 | Coakley et al. |
| 2007/0032708 A1 | 2/2007 | Eghbal et al. |
| 2007/0032709 A1 | 2/2007 | Coakley et al. |
| 2007/0032710 A1 | 2/2007 | Raridan et al. |
| 2007/0032711 A1 | 2/2007 | Coakley et al. |
| 2007/0032712 A1 | 2/2007 | Raridan et al. |
| 2007/0032713 A1 | 2/2007 | Eghbal et al. |
| 2007/0032715 A1 | 2/2007 | Eghbal et al. |
| 2007/0032716 A1 | 2/2007 | Raridan et al. |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |
| 2007/0073125 A1 | 3/2007 | Hoarau et al. |
| 2007/0073126 A1 | 3/2007 | Raridan |
| 2007/0073128 A1 | 3/2007 | Hoarau |
| 2007/0078315 A1 | 4/2007 | Kling et al. |
| 2007/0078316 A1 | 4/2007 | Hoarau |
| 2007/0078317 A1 | 4/2007 | Matlock et al. |
| 2007/0106132 A1 | 5/2007 | Elhag et al. |
| 2007/0123756 A1 | 5/2007 | Kitajima et al. |
| 2007/0129613 A1 | 6/2007 | Rochester et al. |
| 2007/0142717 A1 | 6/2007 | Lowery et al. |
| 2007/0185393 A1 | 8/2007 | Zhou et al. |
| 2007/0208235 A1 | 9/2007 | Besson et al. |
| 2007/0244377 A1 | 10/2007 | Cozad et al. |
| 2007/0260129 A1 | 11/2007 | Chin |
| 2007/0260130 A1 | 11/2007 | Chin |
| 2007/0260131 A1 | 11/2007 | Chin |
| 2007/0276262 A1 | 11/2007 | Banet et al. |
| 2007/0299328 A1 | 12/2007 | Chin et al. |
| 2008/0230363 A1 | 9/2008 | Yang et al. |
| 2008/0262328 A1 | 10/2008 | Adams et al. |

FOREIGN PATENT DOCUMENTS

| | | |
|---|---|---|
| DE | 3405444 | 8/1985 |
| DE | 3516338 | 11/1986 |
| DE | 37 03 458 | 8/1988 |
| DE | 3938759 | 5/1991 |
| DE | 4210102 | 9/1993 |
| DE | 4423597 | 8/1995 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 00194105 | 9/1986 |
| EP | 00204459 | 12/1986 |
| EP | 0 262 779 | 4/1988 |
| EP | 0315040 | 10/1988 |
| EP | 0314331 | 5/1989 |
| EP | 00352923 | 1/1990 |
| EP | 0 360 977 | 4/1990 |
| EP | 00430340 | 6/1991 |
| EP | 0435 500 | 7/1991 |
| EP | 0572684 | 5/1992 |
| EP | 00497021 | 8/1992 |
| EP | 0529412 | 8/1992 |
| EP | 0531631 | 9/1992 |
| EP | 0566354 | 4/1993 |
| EP | 0587009 | 8/1993 |
| EP | 00630203 | 9/1993 |
| EP | 0 572 684 | 12/1993 |
| EP | 00615723 | 9/1994 |
| EP | 00702931 | 3/1996 |
| EP | 724860 | 8/1996 |
| EP | 00724860 | 8/1996 |
| EP | 00793942 | 9/1997 |
| EP | 0 864 293 | 9/1998 |
| EP | 01006863 | 10/1998 |
| EP | 01006864 | 10/1998 |
| EP | 0875199 | 11/1998 |
| EP | 00998214 | 12/1998 |
| EP | 0 898 933 | 3/1999 |
| EP | 0899933 | 3/1999 |
| EP | 01332713 | 8/2003 |

| | | | | | | |
|---|---|---|---|---|---|---|
| EP | 01469773 | 8/2003 | | JP | 24261364 | 9/2004 |
| EP | 1502529 | 7/2004 | | JP | 24290412 | 10/2004 |
| EP | 01491135 | 12/2004 | | JP | 24290544 | 10/2004 |
| EP | 1986543 | 11/2008 | | JP | 24290545 | 10/2004 |
| FR | 2685865 | 1/1992 | | JP | 24329406 | 11/2004 |
| GB | 2 259 545 | 3/1993 | | JP | 24329607 | 11/2004 |
| JP | 63275325 | 11/1988 | | JP | 24329928 | 11/2004 |
| JP | 2013450 | 1/1990 | | JP | 24337605 | 12/2004 |
| JP | 2111343 | 4/1990 | | JP | 24344367 | 12/2004 |
| JP | 02 191434 | 7/1990 | | JP | 24351107 | 12/2004 |
| JP | 2237544 | 9/1990 | | JP | 25034472 | 2/2005 |
| JP | 03 173536 | 7/1991 | | WO | WO 89/09566 | 10/1989 |
| JP | 3170866 | 7/1991 | | WO | WO8909566 | 10/1989 |
| JP | 3245042 | 10/1991 | | WO | WO 90/01293 | 2/1990 |
| JP | 4174648 | 6/1992 | | WO | WO 90/04352 | 5/1990 |
| JP | 4191642 | 7/1992 | | WO | WO 91/01678 | 2/1991 |
| JP | 4332536 | 11/1992 | | WO | WO 91/11137 | 8/1991 |
| JP | 3124073 | 3/1993 | | WO | WO 92/00513 | 1/1992 |
| JP | 5049624 | 3/1993 | | WO | WO 92/21281 | 12/1992 |
| JP | 5049625 | 3/1993 | | WO | WO 93/09711 | 5/1993 |
| JP | 3115374 | 4/1993 | | WO | WO 93/13706 | 7/1993 |
| JP | 05 200031 | 8/1993 | | WO | WO 93/16629 | 9/1993 |
| JP | 2005/200031 | 8/1993 | | WO | WO 94/03102 | 2/1994 |
| JP | 5212016 | 8/1993 | | WO | WO 94/23643 | 10/1994 |
| JP | 06 014906 | 1/1994 | | WO | WO 95/02358 | 1/1995 |
| JP | 06014906 | 1/1994 | | WO | WO 95/12349 | 5/1995 |
| JP | 6016774 | 3/1994 | | WO | WO 95/16970 | 6/1995 |
| JP | 3116255 | 4/1994 | | WO | WO 96/13208 | 5/1996 |
| JP | 6029504 | 4/1994 | | WO | WO 96/39927 | 12/1996 |
| JP | 6098881 | 4/1994 | | WO | WO 97/36536 | 10/1997 |
| JP | 06 154177 | 6/1994 | | WO | WO 97/36538 | 10/1997 |
| JP | 6269430 | 9/1994 | | WO | WO 97/49330 | 12/1997 |
| JP | 6285048 | 10/1994 | | WO | WO 98/17174 | 4/1998 |
| JP | 7001273 | 1/1995 | | WO | WO 98/18382 | 5/1998 |
| JP | 7124138 | 5/1995 | | WO | WO 98/43071 | 10/1998 |
| JP | 7136150 | 5/1995 | | WO | WO 98/51212 | 11/1998 |
| JP | 3116259 | 6/1995 | | WO | WO 98/57577 | 12/1998 |
| JP | 3116260 | 6/1995 | | WO | WO 99/00053 | 1/1999 |
| JP | 7155311 | 6/1995 | | WO | WO 99/32030 | 7/1999 |
| JP | 7155313 | 6/1995 | | WO | WO 99/47039 | 9/1999 |
| JP | 3238813 | 7/1995 | | WO | WO 99/63884 | 12/1999 |
| JP | 7171139 | 7/1995 | | WO | WO 00/21438 | 4/2000 |
| JP | 3134144 | 9/1995 | | WO | WO 00/28888 | 5/2000 |
| JP | 7236625 | 9/1995 | | WO | WO 00/59374 | 10/2000 |
| JP | 7246191 | 9/1995 | | WO | WO 01/13790 | 3/2001 |
| JP | 8256996 | 10/1996 | | WO | WO 01/16577 | 3/2001 |
| JP | 9192120 | 7/1997 | | WO | WO 01/17421 | 3/2001 |
| JP | 10216113 | 8/1998 | | WO | WO 01/47426 | 3/2001 |
| JP | 10216114 | 8/1998 | | WO | WO 01/40776 | 6/2001 |
| JP | 10216115 | 8/1998 | | WO | WO 01/67946 | 9/2001 |
| JP | 10337282 | 12/1998 | | WO | WO 01/76461 | 10/2001 |
| JP | 11019074 | 1/1999 | | WO | WO 02/14793 | 2/2002 |
| JP | 11155841 | 6/1999 | | WO | WO 02/35999 | 5/2002 |
| JP | 11 188019 | 7/1999 | | WO | WO 02/062213 | 8/2002 |
| JP | 11244268 | 9/1999 | | WO | WO 02/074162 | 9/2002 |
| JP | 20107157 | 4/2000 | | WO | WO 02/085202 | 10/2002 |
| JP | 20237170 | 9/2000 | | WO | WO 03/000125 | 1/2003 |
| JP | 21245871 | 9/2001 | | WO | WO 03/001180 | 1/2003 |
| JP | 22224088 | 8/2002 | | WO | WO 03/009750 | 2/2003 |
| JP | 22282242 | 10/2002 | | WO | WO 03/011127 | 2/2003 |
| JP | 23153881 | 5/2003 | | WO | WO 03/020129 | 3/2003 |
| JP | 23153882 | 5/2003 | | WO | WO 03/039326 | 5/2003 |
| JP | 23169791 | 6/2003 | | WO | WO 03/063697 | 8/2003 |
| JP | 23194714 | 7/2003 | | WO | WO 03/073924 | 9/2003 |
| JP | 23210438 | 7/2003 | | WO | WO 04/000114 | 12/2003 |
| JP | 23275192 | 9/2003 | | WO | WO 2004/006748 | 1/2004 |
| JP | 23339678 | 12/2003 | | WO | WO 2004/069046 | 8/2004 |
| JP | 24008572 | 1/2004 | | WO | WO 2004/075746 | 9/2004 |
| JP | 24089546 | 3/2004 | | WO | WO 2005/002434 | 1/2005 |
| JP | 24113353 | 4/2004 | | WO | WO 2005/009221 | 2/2005 |
| JP | 24135854 | 5/2004 | | WO | WO 2005/010567 | 2/2005 |
| JP | 24148069 | 5/2004 | | WO | WO 2005/010568 | 2/2005 |
| JP | 24148070 | 5/2004 | | WO | WO 2005/020120 | 3/2005 |
| JP | 24159810 | 6/2004 | | WO | WO2005053530 | 6/2005 |
| JP | 24166775 | 6/2004 | | WO | WO 2005/065540 | 7/2005 |
| JP | 24194908 | 7/2004 | | WO | WO2006005169 | 1/2006 |
| JP | 24202190 | 7/2004 | | WO | WO2006009830 | 1/2006 |
| JP | 24248819 | 9/2004 | | WO | WO 2006/104790 | 10/2006 |
| JP | 24248820 | 9/2004 | | WO | WO2006109072 | 10/2006 |

| | | |
|---|---|---|
| WO | WO2006110488 | 10/2006 |
| WO | WO2007048039 | 4/2007 |
| WO | WO2007051066 | 5/2007 |
| WO | WO2008019294 | 2/2008 |

OTHER PUBLICATIONS

U.S. Appl. No. 11/716,770, filed Mar. 9, 2007, Hoarau et al.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19$^{th}$ International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings —19$^{th}$ International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20$^{th}$ annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20$^{th}$ Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am. J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part 1: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part 1: Design and Analysis," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved in Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A 10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

* cited by examiner

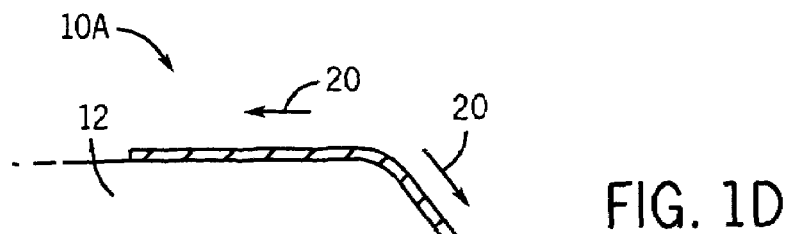
FIG. 1D
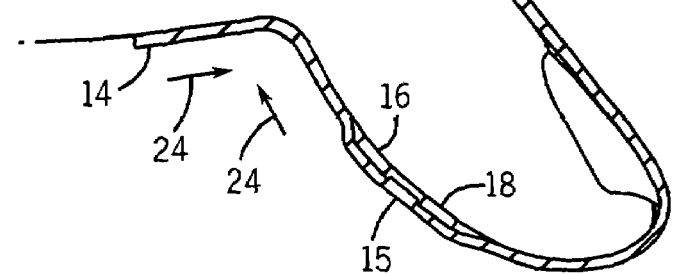
FIG. 2A
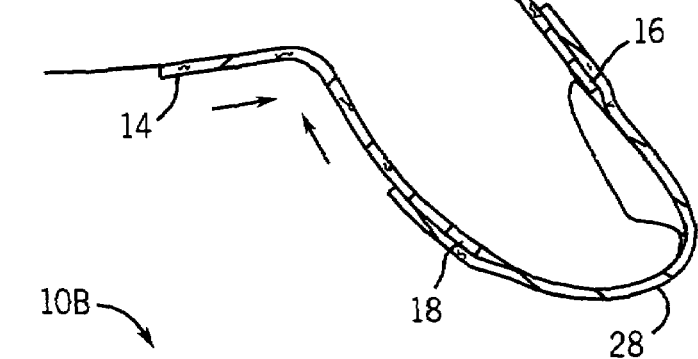
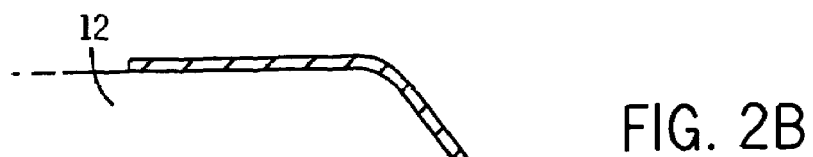
FIG. 2B
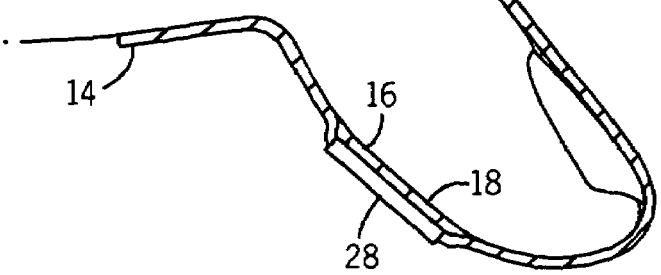

MEDICAL SENSOR FOR REDUCING SIGNAL ARTIFACTS AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits electromagnetic radiation, such as light, through a patient's tissue and that photoelectrically detects the absorption and scattering of the transmitted light in such tissue. One or more of the above physiological characteristics may then be calculated based upon the amount of light absorbed and scattered. More specifically, the light passed through the tissue is typically selected to be of one or more wavelengths that may be absorbed and scattered by the blood in an amount correlative to the amount of the blood constituent present in the tissue. The measured amount of light absorbed and scattered may then be used to estimate the amount of blood constituent in the tissue using various algorithms.

Pulse oximetry readings measure the pulsatile, dynamic changes in amount and type of blood constituents in tissue. Other events besides the pulsing of arterial blood may lead to modulation of the light path, direction, and the amount of light detected by the sensor, creating error in these measurements. Pulse oximetry measurements may be affected by various noise sources, and various types of events may cause artifacts that may obscure the blood constituent signal. For example, signal artifacts may be caused by moving a sensor in relation to the tissue, by increasing or decreasing the physical distance between emitters and detectors in a sensor, by changing the direction of emitters or detectors with respect to tissue or each other, by changing the angles of incidence and interfaces probed by the light, by directing the optical path through different amounts or types of tissue, or by expanding, compressing or otherwise altering tissue near a sensor. In the emergency room, critical care, intensive care, and trauma center settings, where pulse oximetry is commonly used for patient monitoring, the wide variety of sources of motion artifacts includes moving of a patient or the sensor by healthcare workers, physical motion of an unanaesthetised or ambulatory patient, shivering, seizures, agitation, response to pain and loss of neural control. These motions oftentimes have similar frequency content to the pulse, and may lead to similar or even larger optical modulations than the pulse.

Two categories of pulse oximetry sensors in common use may be classified by their pattern of use: the disposable and the reusable sensor. Disposable sensors are typically flexible bandage-type structures that may be attached to the patient with adhesive materials, providing a contact between the patient's skin and the sensor components. Disposable sensors have multiple advantages, including ease of conformation to the patient. However, the flexible nature of disposable sensors renders them susceptible to signal artifacts caused by mechanical deformation of the sensor, which changes the amount of light detected. Reusable sensors, often semi-rigid or rigid clip-type devices, are also vulnerable to signal artifacts. Both categories of sensors may have modulations of detected light induced by the physical motion of the sensor components with respect to each other and the tissue.

Signal artifacts may sometimes be addressed by signal processing and filtering to mitigate the effects of motion after the motion has occurred. However, signal processing algorithms to filter out motion artifacts after they have occurred may not filter out all type of artifacts. For example, certain types of regular movements, such as tapping, may not be interpreted by a signal artifact filter as noise. Thus, it would be desirable to provide a sensor that prevents, reduces the occurrence of, or mitigates movements that may lead to motion artifacts. Such a sensor may incorporate elements which enhance patient comfort without reducing the sensor's resistance to movement or outside forces.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body comprising an elastic material; and an emitter and a detector disposed on the sensor body, wherein sensor body is substantially inelastic in at least part of a region of the sensor body connecting the emitter and the detector.

There is also provided a pulse oximetry system that includes: a pulse oximetry monitor; and a pulse oximetry sensor adapted to be operatively coupled to the monitor. The sensor includes a sensor body comprising an elastic material; and an emitter and a detector disposed on the sensor body, wherein sensor body is substantially inelastic in at least part of a region of the sensor body connecting the emitter and the detector.

There is also provided a method that includes: applying a sensor body comprising an emitter and a detector to a patient's tissue; and stretching an elastic portion of a sensor body in response to a movement of the tissue, wherein the optical distance between the emitter and the detector remains substantially fixed.

There is also provided a method of manufacturing a sensor that includes: providing a sensor body comprising an elastic material; and providing an emitter and a detector disposed on the sensor body, wherein sensor body is substantially inelastic in at least part of a region of the sensor body connecting the emitter and the detector.

There is also provided a sensor that includes: a sensor body adapted to expand in response to a biasing force; and an emitter and a detector disposed on the sensor body, wherein the sensor body is adapted to fix the optical distance between the emitter and the detector.

There is also provided a sensor that includes: a sensor body comprising at least one elastic electronic component; and an emitter and a detector disposed on the sensor body.

There is also provided a system that includes: a monitor; and a sensor adapted to be operatively coupled to the monitor, the sensor including: a sensor body comprising at least one elastic electronic component; and an emitter and a detector disposed on the sensor body.

There is also provided a method of response to movement of a sensor that includes: applying a sensor body comprising an emitter and a detector to a patient's tissue; and stretching an elastic electronic component of a sensor body in response to a movement of the tissue, wherein the optical distance between the emitter and the detector remains substantially fixed.

There is also provided a method of manufacturing a sensor, including: providing a sensor body comprising at least one elastic electronic component; and providing an emitter and a detector disposed on the sensor body.

There is also provided a sensor that includes: a sensor body; an emitter and a detector disposed on the sensor body; and an electronic component operatively connected to the emitter or the detector adapted to expand in response to a biasing force.

There is also provided a sensor that includes: a sensor body comprising an exterior surface and a tissue-contacting surface; at least one sensing element disposed on the sensor body; a cable adapted to be electrically coupled to the sensing element; and a cable guide disposed on exterior surface of the sensor body, wherein the cable guide is adapted to hold the cable in a predetermined position on the sensor body.

There is also provided a pulse oximetry system that includes: a pulse oximetry monitor; and a pulse oximetry sensor adapted to be operatively coupled to the monitor. The sensor includes: a sensor body comprising an exterior surface and a tissue-contacting surface; at least one sensing element disposed on the sensor body; a cable adapted to be electrically coupled to the sensing element; and a cable guide disposed on exterior surface of the sensor body, wherein the cable guide is adapted to hold the cable in a predetermined position on the sensor body.

There is also provided a method that includes: applying a sensor body comprising a sensing component to a patient's tissue; and securing a sensor cable that is operatively connected to the sensing component in a predetermined position on a sensor body with a cable guide.

There is also provided a method of manufacturing a sensor that includes: providing a sensor body comprising an exterior surface and a tissue-contacting surface; providing at least one sensing element disposed on the sensor body; providing a cable adapted to be electrically coupled to the sensing element; and providing a cable guide disposed on the exterior surface of the sensor body, wherein the cable guide is adapted to hold the cable in a predetermined position on the sensor body.

There is also provided a sensor that includes: a sensor body; at least one sensing element disposed on the sensor body; and a cable adapted to be electrically coupled to the sensing element, wherein the cable is disposed along the sensor body in a curvilinear configuration.

There is also provided a system that includes: a monitor; and a sensor adapted to be operatively coupled to the monitor. The sensor includes: a sensor body; at least one sensing element disposed on the sensor body; and a cable adapted to be electrically coupled to the sensing element, wherein the cable is disposed along the sensor body in a curvilinear configuration.

There is also provided a method that includes: electrically coupling a sensing element to a monitor with a cable, wherein sensing element is disposed on the sensor body and wherein the cable is disposed along the sensor body in a curvilinear configuration.

There is also provided a method that includes: providing a sensor body; providing at least one sensing element disposed on the sensor body; and providing a cable adapted to be electrically coupled to the sensing element, wherein the cable is disposed along the sensor body in a curvilinear configuration.

There is also provided a sensor that includes: an emitter and a detector disposed on a substantially rigid substrate, wherein the substantially rigid substrate is adapted to hold the emitter and detector at a substantially fixed optical distance relative to one another when the sensor is applied to a patient.

There is also provided a system that includes: a monitor; and a sensor adapted to be operatively coupled to the monitor. The sensor includes: an emitter and a detector disposed on a substantially rigid substrate, wherein the substantially rigid substrate is adapted to hold the emitter and detector at a substantially fixed optical distance relative to one another when the sensor is applied to a patient.

There is also provided a method that includes: fixing the optical distance between an emitter and a detector relative to one another, wherein the emitter and the detector are disposed on a substantially rigid substrate.

There is also provided a method of manufacturing a sensor that includes:
providing a substantially rigid substrate on which an emitter and a detector are disposed, wherein the substantially rigid substrate is adapted to hold the emitter and the detector at a substantially fixed optical distance.

BRIEF DESCRIPTION OF THE DRAWINGS

Advantages of the invention may become apparent upon reading the following detailed description and upon reference to the drawings in which:

FIG. 1D illustrates a cross-sectional view of an alternative embodiment of a sensor using reflectance-type sensing elements;

FIG. 2A illustrates a cross-sectional view of an exemplary embodiment of an elastic transmission-type bandage-style sensor applied to a patient's digit, whereby the sensor includes a stiffening member;

FIG. 2B illustrates a cross-sectional view of an exemplary embodiment of an elastic reflectance-type bandage-style sensor applied to a patient's digit, whereby the sensor includes a stiffening member;

DETAILED DESCRIPTION OF SPECIFIC EMBODIMENTS

Figure 1A:
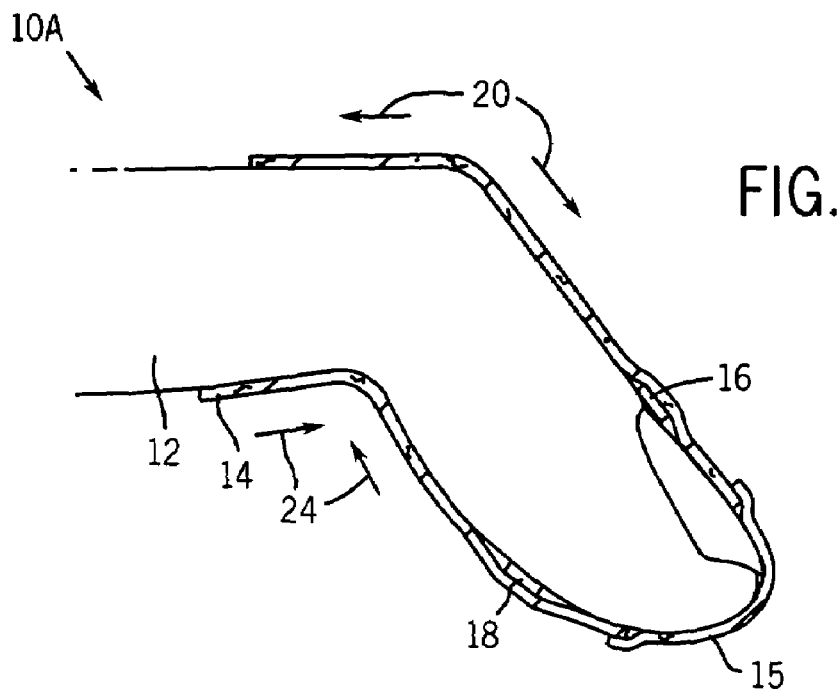
FIG. 1A illustrates a cross-sectional view of an exemplary embodiment of a transmission-type bandage-style sensor with an elastic sensor body.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present technique, sensors for pulse oximetry or other applications utilizing spectrophotometry are provided that reduce signal artifacts by reducing the occurrence of tissue deformation, such as compression or discoloration, associated with the movement of a patient's tissue relative to the sensor or the movement of the sensor elements relative to one another. For example, sensors are provided herein that include elastic materials that may accommodate patient movement. The sensors that include elastic materials are configured to reduce pressure from the sensor on the tissue during such movement. Sensors are also provided in which a sensor cable is directed or arranged in relation to the sensor body such that the pressure or weight of the cable on a patient's tissue is reduced.

Signal artifacts in pulse oximetry may be caused by patient movement, including movement of the optically probed tissue within the sensor. Although a typical conformable sensor may be sufficiently flexible to wrap around a patient's tissue, such a flexible yet inelastic sensor will nonetheless provide resistance to the tissue as it moves within the sensor. As a patient's tissue presses against an inelastic sensor's surfaces, such as the sensor body, the sensing elements, and the cable, the pressure of the sensor against the tissue may result in temporary changes to the tissue. Such changes in response to pressure include blanching of the skin, coloring of the skin due to blood pooling, creasing of the skin in response to bending at joints, and spreading or compression of the tissue. These variations in tissue geometry and color may result in signal artifacts. For example, coloring of the skin may result in increased absorption of light by the tissue that is not related to a physiological constituent. Alternatively, blanching of the skin may lead to shunting of light through exsanguinated or partially exsanguinated tissue. Additionally, although an inelastic sensor may not expand or contract in response to patient movement, such a sensor may yet be vulnerable to mechanical deformation that may change the geometry of the sensing elements relative to one another. As bandage-type inelastic sensors are generally relatively flexible, though inelastic, such sensors may twist or come away from the skin, which may alter the geometry of the sensing elements. Because medical sensors are often used in settings where it is difficult to prevent patient motion, it is desirable to provide a mechanism for reducing the effects of patient and/or sensor motion on the sensor signals.

Figure 1B:
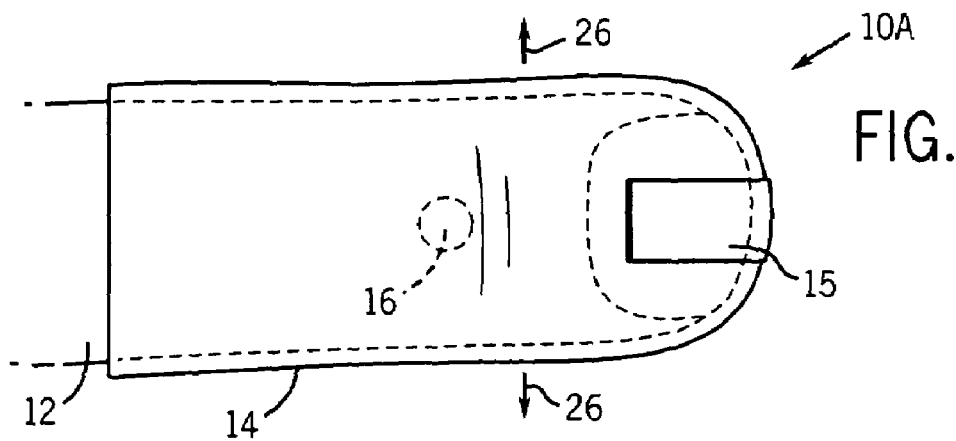
FIG. 1B illustrates a top view of the sensor of FIG. 1A applied to a patient digit.
Figure 1C:
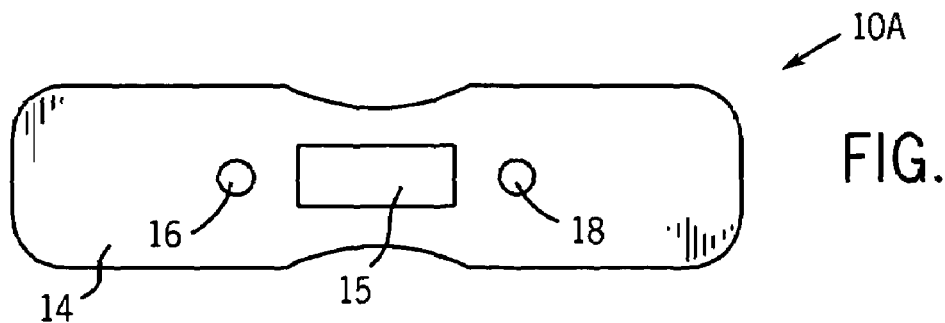
FIG. 1C illustrates a perspective view the sensor of FIG. 1A.

Sensors are disclosed herein that include elastic materials and that may reduce the effect of patient motion within a sensor. FIG. 1A illustrates a cross-sectional view of an exemplary bandage-type sensor 10A appropriate for use on a patient's finger 12. The sensor 10A has an elastic sensor body 14. The elastic sensor body 14 may accommodate movement of the finger 12 with the sensor 10A. An inelastic portion 15 disposed on the sensor body in a region between the emitter 16 and the detector 18 may serve to reduce or eliminate changes in the optical distance due to stretching of the elastic sensor body 14. The inelastic portion 15 does not stretch in response to the patient movement, and thus the accommodation of the patient movement by the elastic sensor body 14 may have a reduced effect or no effect on the position of the emitter 16 and the detector 18 relative to one another, as discussed in more detail below. As depicted, the finger 12 is flexed, causing the elastic sensor body 14 to stretch and expand, indicated by arrows 20, in an area corresponding to the nail side of the finger joint. In the area corresponding to the palm side of the finger joint 22, the elastic sensor body may contract, as indicated by arrows 24. As shown in FIG. 1B, a top view of the sensor 10A, the elastic sensor body 14 may also stretch to accommodate spreading of the tissue in the fingertip region of the finger during flexing, indicated by arrows 26. Alternatively, in other embodiments (not shown) the tissue in the fingertip region may spread or expand when the finger 12 is pressed against a rigid object. Hence, as the finger 12 moves, the elastic sensor body 14 is able to conform to the tissue as it changes shape while the inelastic portion 15 provides stability to the emitter 16 and the detector 18. FIG. 1C is a top view of the sensor 10A showing the inelastic portion 15 in the region of the sensor body 14 between the emitter 16 and the detector 18. In an alternative embodiment, the sensor 10A may be a reflectance-type sensor, as shown in FIG. 1D. In such an embodiment, the emitter 16 and the detector 18 are positioned side-by-side. Such a sensor may provide certain advantages. For example, the emitter 16 and the detector 18 may be manufactured as a single, smaller part as compared to a transmission-type sensor.

The term elastic as used herein may describe any material that, upon application of a biasing force, is able to be stretched at least about 100% (i.e., to a stretched, biased length that is at least about 100% of its relaxed unbiased length). Many elastic materials may be elongated by much more than 400% and may, for example, be elongated at least 500%, 600% or more. Further, upon release of the biasing force, the elastic material is able to substantially recover its unbiased length. In certain embodiments, upon release of the biasing force, the elastic material returns to a length that is 120% or less of its original unbiased length. For example, a hypothetical elastic material that is one inch in length is able to be stretched to at least 2.00 inches, and when the stretch is released, the material return to a length that is less than 1.20 inches. Exemplary elastic materials may include spandex or spandex blends. Another appropriate elastomer is Rx715P, available from Scapa (Windsor, Conn.). In certain embodiments, it is contemplated that the elastic material may be a woven or knit material. In one embodiment, the elastic material may be woven or otherwise configured such that the material has a one-way stretch along a single axis. For example, a one-way elastic material may stretch lengthwise down the finger over the joints as the finger is bent. In other embodiments, the elastic material may be an elastomer, such as a polymer-based material. Appropriate materials also include natural rubber, silicone rubber, neoprene, and synthetic polymers.

In certain embodiments, sensors that include elastic materials may provide a compressive force to the tissue to which they are applied. The compressive force provided by a sensor according to the present techniques can be varied to provide an appropriate level of pressure to the tissue. In certain embodiments, a sensor including an elastic material may provide sufficient pressure to the tissue so that the applied pressure exceeds the typical venous pressure of a patient, but does not exceed the diastolic arterial pressure. A sensor that applies a pressure greater than the venous pressure may squeeze excess venous blood from the optically probed tissue, thus enhancing the sensitivity of the sensor to variations in the arterial blood signal. Since the pressure applied by the sensor is designed to be less than the arterial pressure, the application of pressure to the tissue does not interfere with the arterial pulse signal. Typical venous pressure, diastolic arterial pressure and systolic arterial pressure are typically less than 10-35 mmHg, 80 mmHg, and 120 mmHg, respectively, although these pressures may vary because of the location of the vascular bed and the patient's condition. In certain embodiments, the sensor may be adjusted to overcome an average pressure of 15-30 mmHg. In other embodiments, low arterial diastolic blood pressure (about 30 mmHg) may occur in sick patients. In such embodiments, the sensor may remove most of the venous pooling with light to moderate pressure (to overcome about 15 mmHg).

Sensors that include elastic materials as described herein may also include an inelastic portion 15 disposed on the sensor body that may reduce or eliminate changes in optical distance between the sensing elements due to sensor bending or stretching in response to movement. The inelastic portion 15 may include any substantially inelastic material and relatively inflexible material, including substantially inelastic stiffened paper, metal, or polymeric material. Generally, a substantially inelastic portion is unable to be elongated 50% or more of its total length. Thus, a hypothetical inelastic material one inch in length is not able to be stretched elastically to 1.50 inches or more without causing damage or permanent deformation to the material.

The inelastic portion 15 may provide stability to the emitter 16 and detector 18 by mitigating the effects of stretching the elastic sensor body 14 on the optical distance. Reducing or controlling changes in the optical distance may include reducing any change in position or geometry of the sensing elements of a sensor. More specifically, a change in optical distance may involve any change in optical geometry, such as a change in the path length, a change in the relative angle of the sensing elements relative to one another, and/or a change in the angle of the sensing elements relative to the tissue. As sensors do not typically emit nor detect light omnidirectionally, any motions that lead to variations in angle of sensor components may alter the amount of light detected, and may force detected light through different portions of tissue. In any case, variability in the optical path length can cause signal artifacts and obscure the desired pulse oximetry signal. Thus, it is desirable that a sensor's emitter(s) and detector(s) experience a minimum of movement relative to one another and relative to the patient's tissue.

In an alternate embodiment, a cross-sectional view of an elastic sensor 10B is illustrated in FIG. 2A in which an inelastic portion of the sensor 10B includes a stiffening member 28. The stiffening member 28 is disposed on an elastic sensor body 14 in a region between the emitter 16 and detector 18. The stiffening member 28 may be constructed from any suitable material that functions to hold the emitter 16 and the detector 18 at a substantially fixed optical distance when the sensor 10B is applied to a patient. For example, a suitable stiffening member 28 may be metal, plastic or polymeric material, or cardboard. In certain embodiments, suitable metals include aluminum or brass. The stiffening member 28 may be in the shape of a strip, wire, or mesh that can be easily adapted for use with an elastic sensor body 14. The stiffening member 28 may adapted to be bent, shaped, activated, or applied to a conformable elastic sensor body 14 in order to hold an emitter 16 and a detector 18 at a substantially fixed optical distance. The stiffening member 28 may be sized to form a strip that is generally in the area surrounding the emitter 16 and the detector 18. A stiffening member 28 need not be solid, but may also be a fluid or other non-solid material that stabilizes the optical distance between an emitter 16 and a detector 18. For example, a stiffening member 28 may include a bladder that is adapted to hold a fluid. In certain embodiments, it may be desirable employ a gas or gas mixture as part of the stiffening member 28 for reasons related to cost, manufacturing convenience, and total sensor weight.

Figure 2C:
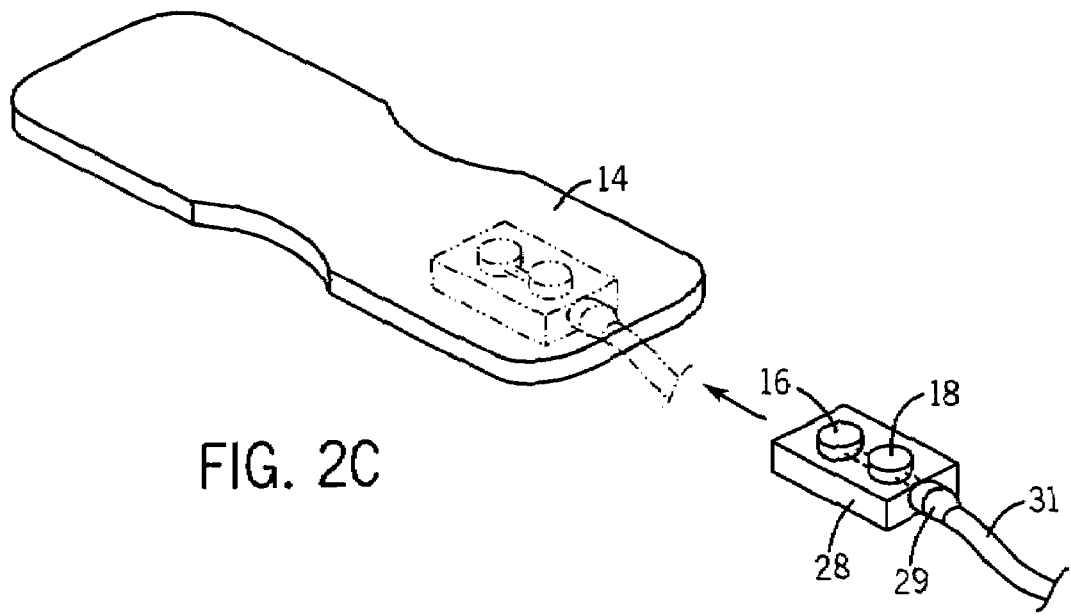
FIG. 2C illustrates an embodiment of the sensor of FIG. 2B, whereby the stiffening member and sensing components may be a unitary assembly.

FIG. 2B illustrates an embodiment in which the sensor 10B is configured to be in reflectance mode. In certain embodiments, the emitter 16 and the detector 18 may both be disposed on or within the stiffening member 28, as shown in FIG. 2C. In FIG. 2C, a sensing component assembly 25 is formed by the emitter 16 and detector 18, which are embedded in the stiffening member 28 and are connected to a cable 31 by wires 29. The sensing component assembly 25 may be disposed on the elastic sensor body 14, adhesively or otherwise. In an alternate embodiment (not shown), the sensing component assembly 25 may be applied to a patient's tissue with elastic tape or bandages.

Figure 3A:
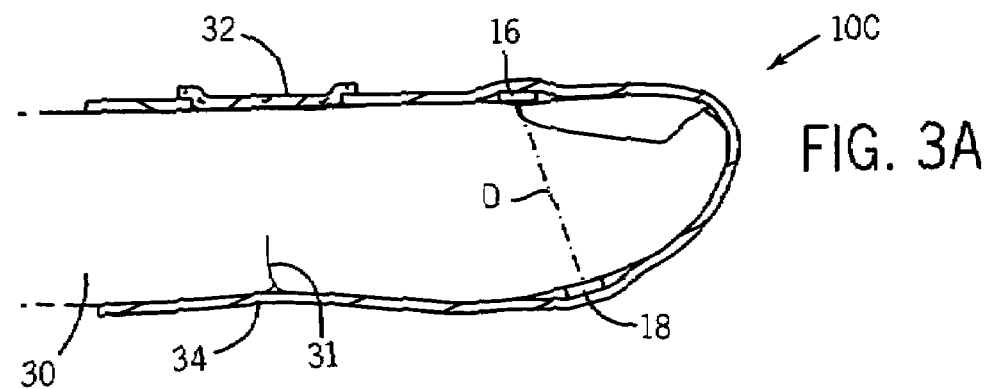
FIG. 3A illustrates a cross-sectional view of an alternate exemplary embodiment of a bandage-style sensor with an inelastic sensor body with elastic portions disposed proximate to the finger joint.
Figure 3B:
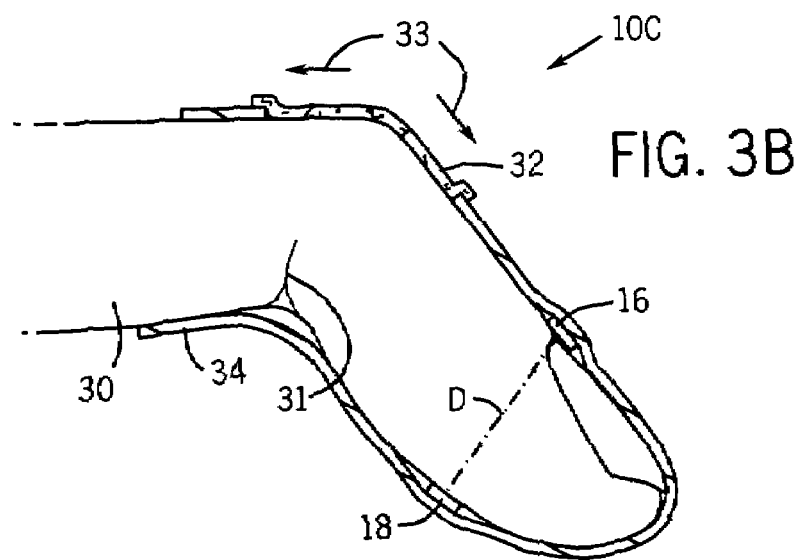
FIG. 3B illustrates a cross-sectional view of the sensor of FIG. 3A with the finger joint flexed.

In certain embodiments, a sensor may include elastic materials only in specific portions of the sensor. For example, it may be desirable to design a finger sensor with elastic portions that correspond to areas of a finger that are likely to move, such as joints. FIG. 3A illustrates a bandage-type sensor 10C applied to a patient's finger 30. The sensor 10C includes an elastic portion 32 disposed on an inelastic sensor body 34. The elastic portion 32 corresponds to the top of a finger joint 31. As depicted in FIG. 3B by arrows 33, when the finger 30 bends at the joint 31, the elastic portion 32 stretches to accommodate the movement. However, the optical distance, indicated by dashed line "D", between the emitter 16 and the detector 18 remains substantially fixed.

It should be understood the ratio of elastic portions and inelastic portions of a sensor body may be varied according to the activity level of the patient wearing the sensor. For example, for a very active patient, it may be advantageous to apply a sensor having more elastic portions, such as a ratio of elastic portions to inelastic portions of greater than one. In certain embodiments, it is contemplated that total elastic surface area of a sensor body may be at least about 5%, and typically in a range from about 10% to about 95%.

Figure 4:
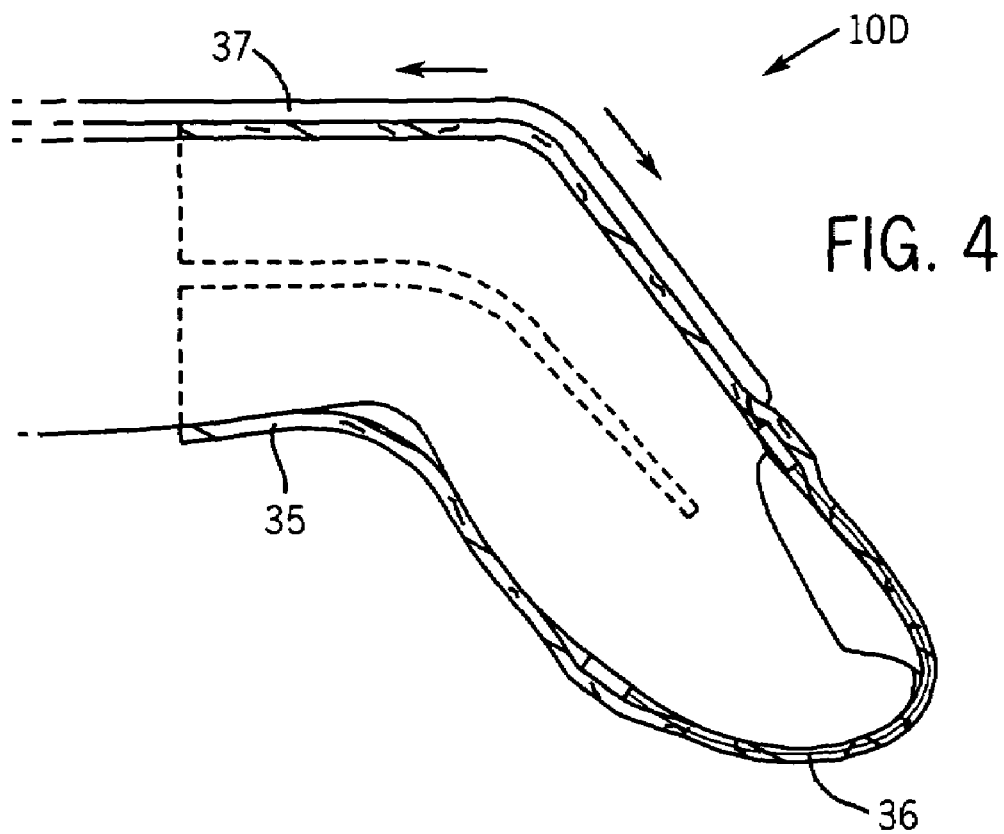
FIG. 4 illustrates a side view of an exemplary embodiment of a sensor with an elastic sensor cable.

In certain embodiments, a sensor may include elastic electrical components, including sensor cable components or wires. FIG. 4 illustrates a side view of a sensor 10D with an elastic cable 37 disposed on the sensor body 35. As the finger flexes, the elastic cable 37 is able to accommodate the flexing motion. The elastic elastic components, such as the elastic cable 37, may include transducers and/or electronic circuits integrated onto an elastic polymer that include elastic metal that remain electrically conducting even under large and repeated stretching and relaxation. Suitable elastic polymeric materials include silicone rubber, such as polydimethyl siloxane (PDMS) and acrylic rubber. Electrically conductive materials useful for elastic conductive films include metallic conducting materials such as copper, silver, gold, aluminum and the like. Alternatively, electrically conductive materials include organic conducting materials such as polyaniline. Suitable electrically conductive materials include a semiconductor, either inorganic like silicon or indium tin oxide, or organic-like pentacene or polythiophene. Alternatively, the electrically conductive materials can be alloys instead of stoichiometric elements or compounds. The elastic conductive film can be formed on elastic polymeric substrate by electron beam evaporation, thermal evaporation, sputter deposition, chemical vapor deposition (CVD), electroplating, molecular beam epitaxy (MBE) or any other conventional means.

Sensors are also disclosed herein in which a sensor cable is routed away from areas of the sensor body that may be subject to tissue pressure or movement. Typically, a sensor cable is embedded in the sensor body and runs through the sensor body along an imaginary axis connecting the sensor's emitter and detector. When such a sensor is applied to a patient's finger, the cable wraps around the fingertip region and runs along the top of the digit. As the finger flexes, the relatively rigid and inelastic cable resists the flexing motion, which may result in tissue discoloration, such as reddening or exsanguinations, or deformation in the area where the tissue pushes against the cable. Similarly, when the finger taps against a rigid object, the fingertip region is pushed against the relatively rigid sensor cable, and the tissue may experience discoloration or deformation. As changes in tissue color and geometry may lead to signal artifacts, it is desirable to alter the arrangement of the sensor cable in relation to the sensor body to mitigate such signal interference.

Figure 5A:
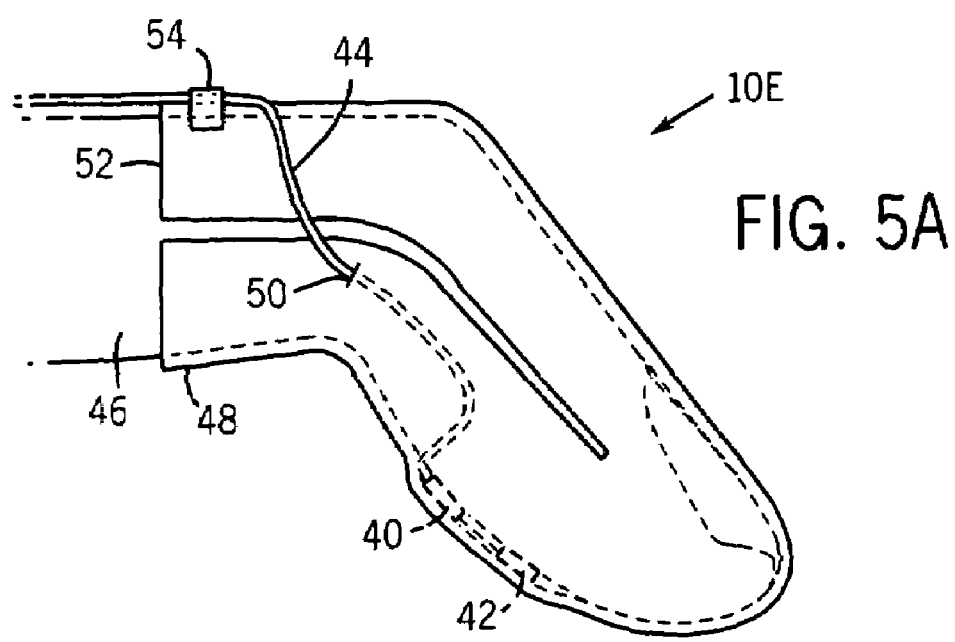
FIG. 5A illustrates a side view of an exemplary embodiment of a sensor whereby the sensor cable is disposed along the side of the finger and secured with a cable guide.
Figure 5B:
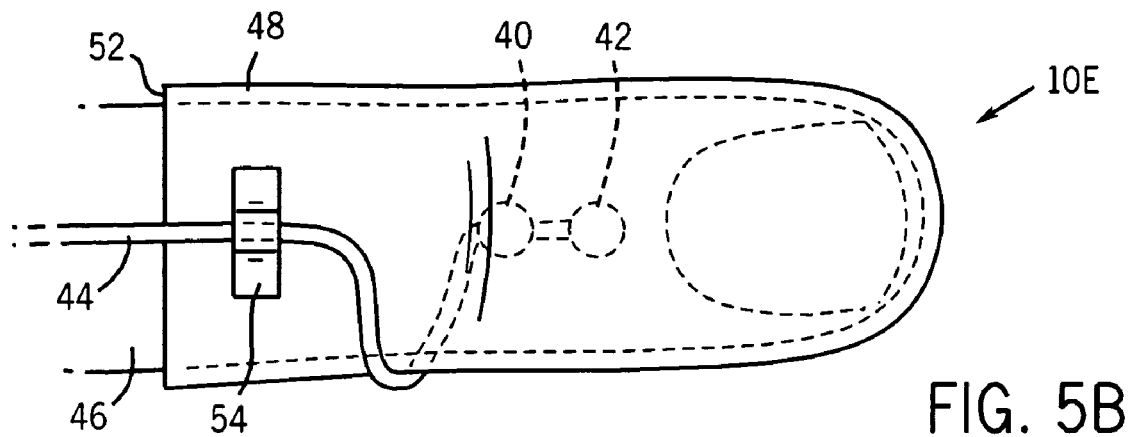
FIG. 5B illustrates a top view of the sensor of FIG. 5A.

Sensors are provided herein that include cables with non-axial or curvilinear paths in relation to the sensor body. FIG. 5A illustrates a side view reflectance-type sensor 10E applied to a patient's finger 46. FIG. 5B is a top view of the sensor 10E. The emitter 40 and the detector 42 are operatively connected to a sensor cable 44. The sensor cable 44, rather than wrapping around the tip of the finger 46, follows a nonlinear, i.e. non-axial, route within the sensor body 48. The cable 44 is partially embedded in the sensor body 48, and may emerge from the sensor body 48 at a site 50 that is not on the outer perimeter 52. Alternatively, the site 50 may be along the outer perimeter 52. When the cable 44 emerges from the sensor body 48, it may be wrapped around the top of the finger 46 and secured with a cable guide 54, as shown in FIG. 5B. The cable guide 54 may be any suitable securing mechanism, include a loop, slot, snap, adhesive, or hook and loop fastener. Further, the cable guide 54 may be elastic in certain embodiments, allowing it to stretch tightly over the cable 44 to provide a secure hold.

Figure 5C:
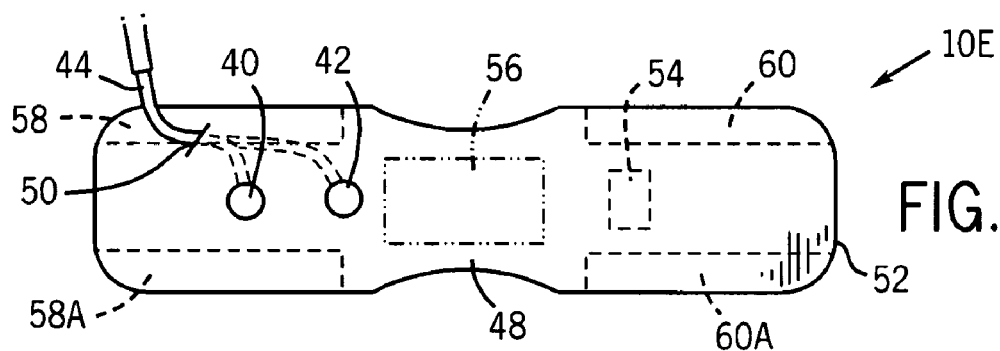
FIG. 5C illustrates a perspective view of the sensor of FIG. 5A.

Generally, the cable 44 may be routed along the sensor body 48 in any configuration associated with a mitigation of signal artifacts. For example, the cable 44 may be routed along the sensor body 48, e.g. embedded within or disposed on a surface of the sensor body 48, to avoid the region 56 of the sensor body 48 corresponding with the fingertip region of the finger in order to mitigate signal artifacts associated with scratching or tapping. In order to mitigate motion artifacts associated with bending at a joint, the cable 44 may routed along the sensor body 48 to avoid the most dynamic regions of the finger 46, such as the top and bottom of the joint. In such an embodiment, the cable 44 may be routed in an area corresponding to side regions 58 and 60 of the finger 46, as shown in FIG. 5C. It should be understood that in another embodiment, the cable may be routed along the sensor body in an area corresponding to side regions 58A and 60A, corresponding to an alternative side of the finger.

Figure 6A:
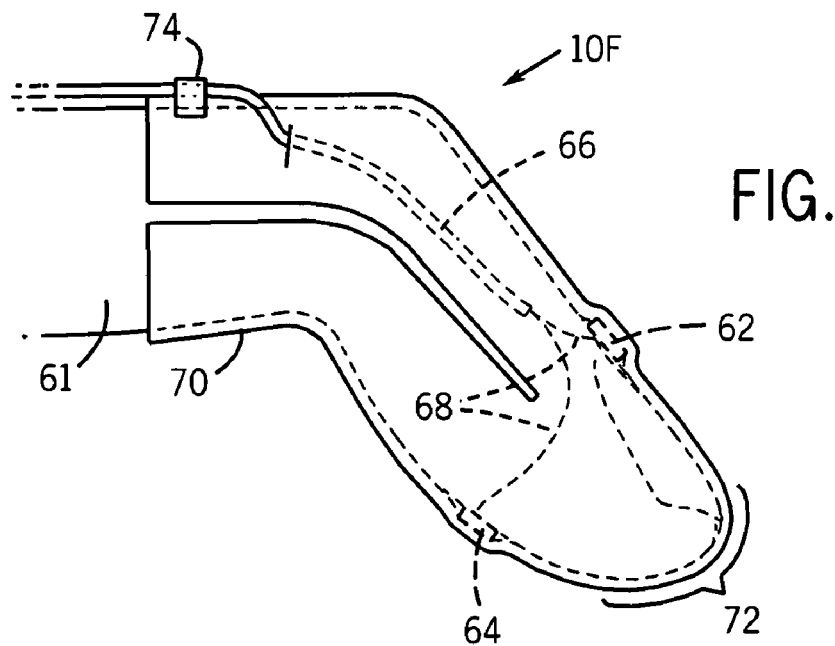
FIG. 6A illustrates a side view of an embodiment of an exemplary sensor applied to a patient's finger with a sensor cable disposed on the sensor body in a configuration that avoids the fingertip region.
Figure 6B:
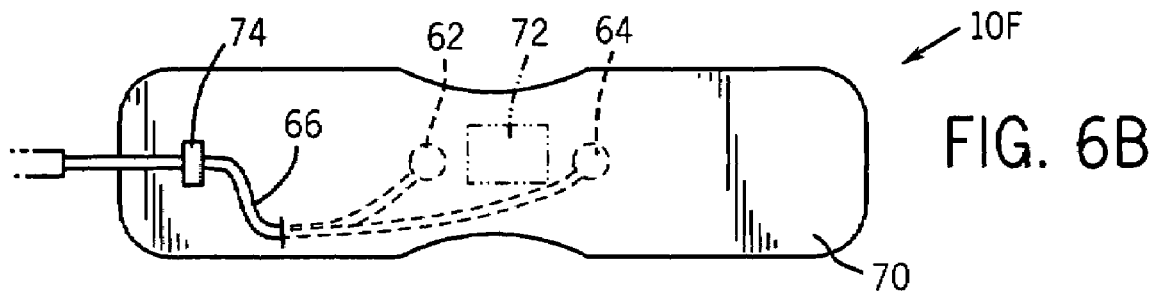
FIG. 6B illustrates a perspective view of the sensor of FIG. 6A.

Such an arrangement of the sensor cable may also be advantageous in a transmission-type sensor, in which a sensor's emitter 62 and detector 64 lie on opposing side of the tissue. FIG. 6A illustrates a sensor 10F of this type applied to a patient's finger 61. Wire leads 68 from an emitter 62 and a detector 64 converge at a sensor cable 66. FIG. 6B illustrates a perspective view of the sensor 10F. The wire leads 68 and sensor cable 66 are arranged along the sensor body 70 such that the sensor cable 66 is not disposed within a region 72 of the sensor body 70 corresponding with the fingertip region of the finger 61 in order to mitigate signal artifacts associated with scratching or tapping. The cable 66 may be wrapped around the finger 61 and secured with a cable guide 74. In an alternate embodiment (not shown), the wire leads 68, which are relatively thin, may be arranged to run along the fingertip region 72 and then along the sensor body 70 to join the sensor cable 66, which is not disposed in the fingertip region 72.

Figure 7A:
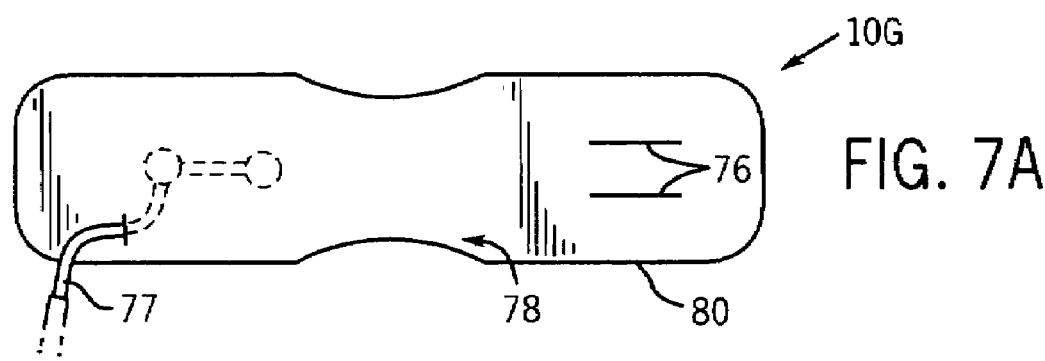
FIG. 7A illustrates a perspective view of an embodiment of an exemplary sensor with alignment indices for the sensor cable.
Figure 7B:
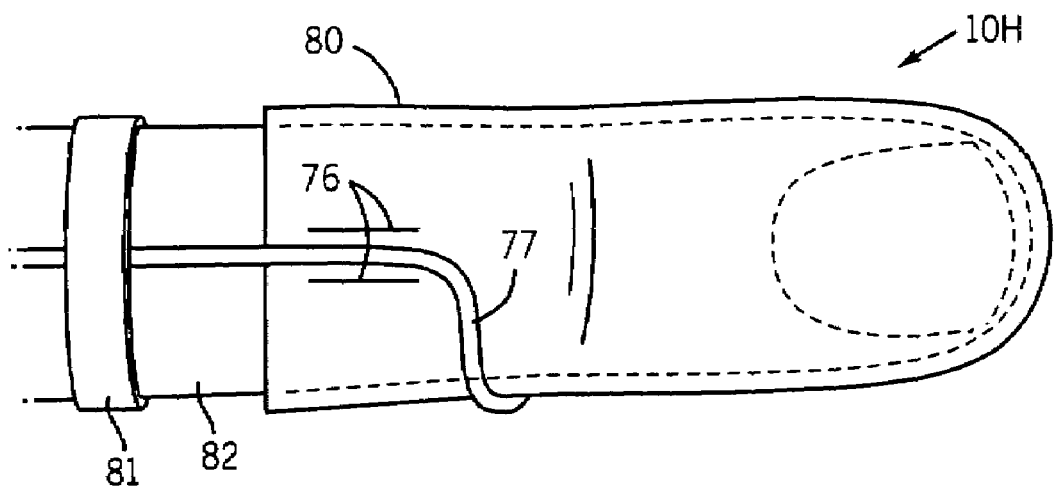
FIG. 7B illustrates a top view of the sensor of FIG. 7A applied to a patient's finger and secured with adhesive bandages such that the sensor cable is aligned with the alignment indices.

In certain embodiments, it may be advantageous for a sensor cable to be secured by a healthcare worker with tape or bandages on an appropriate location of a sensor body. FIG. 7A illustrates a sensor 10G which includes alignment indices 76 for a sensor cable 77 on a non-tissue contacting surface 78 of the sensor body 80. FIG. 7B shows the sensor 10G applied to a patient's finger 82. When the sensor 10G is applied, the sensor cable 77 may be arranged along the non-tissue contacting surface 78 of the sensor body 80 by a healthcare worker. The alignment indices 76 provide an indication where the sensor cable 77 should lie against the sensor body 80 prior to being secured by bandages 81, as shown, or by tape or other securing mechanisms. Alternatively, the healthcare worker may wish to wrap the sensor cable 77 along the sensor body 80 in such a manner as to minimize the pressure of the sensor cable 77 against the patient's finger 82. In such an embodiment (not shown), the sensor cable 77 may be loosely wrapped such the sensor cable 77 is not flush against the sensor body 80.

Figure 8:
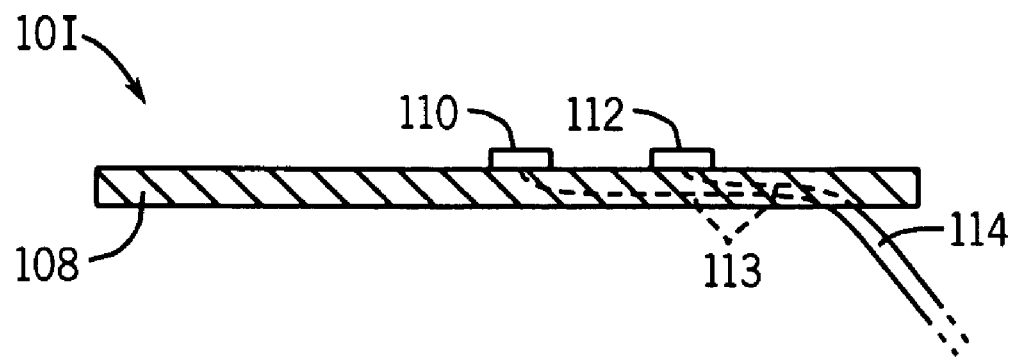
FIG. 8 illustrates a cross-sectional view of an embodiment of an exemplary sensor with a sensor cable that extends at an angle away from the sensor body.

FIG. 8 illustrates a sensor 10J with an alternate sensor cable configuration. The sensor cable 114 is electrically connected to the emitter 110 and detector 112 by wire leads 113. The wire leads 113 join the sensor cable 114 within the sensor body 108, and the sensor cable 114 emerges from the sensor body 108 at an angle that is not in line with the plane of the sensor body 108 when the sensor body 108 is laid flat. Although the sensor body 108 generally assumes a more complex, nonplanar geometry after application to a patient's tissue, the result of this configuration is that the sensor cable 114 is directed away from the tissue. Thus, the sensor cable 114 may be less likely to interfere with patient motion or to compress the tissue. Such a configuration may be applied to the patient's tissue in any configuration. For example, the sensor 10J may be applied such that the sensor cable 114 emerges from the sensor body 108 along the sides of the patient's finger. In such an embodiment, the sensor cable 114 emerges and is at an angle such that the sensor cable 114 is not flush against the tissue.

Figure 9:
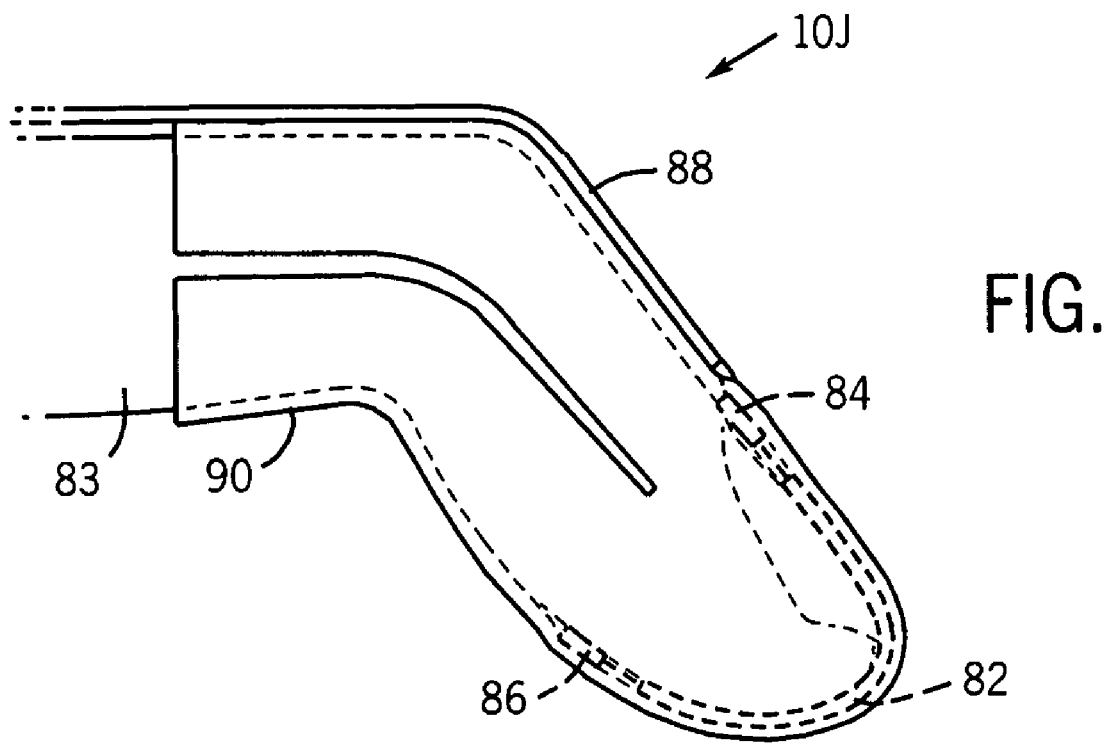
FIG. 9 illustrates a side view of an embodiment of an exemplary sensor with a flexible circuit connecting the emitter and detector.

In another embodiment, it may be advantageous to replace all or part of a sensor cable with a lightweight flexible circuit. FIG. 9 illustrates an exemplary sensor 10I that includes a flexible circuit 82 electrically connecting the emitter 84 and the detector 86 to a sensor cable 88. The flexible circuit 82 includes conductive elements printed on a flexible, non-conductive substrate, such as polyimide or polyester, in order to provide electrical communication to and from the emitter 84 and the detector 86. The flexible circuit 82 may be embedded in the sensor body 90 in a region between the emitter 84 and the detector 86. As shown in FIG. 8, the flexible circuit 82 bends easily around the finger 83. As the flexible circuit 82 has few rigid surfaces, the tissue may experience fewer discoloration or deformation events associated with signal artifacts when pressed against the flexible circuit 82 embedded in the sensor body 90. The flexible circuit 82 may include at least one connection point that is suitable for electrically coupling the flexible circuit 82 to the sensor cable 88.

Figure 10:
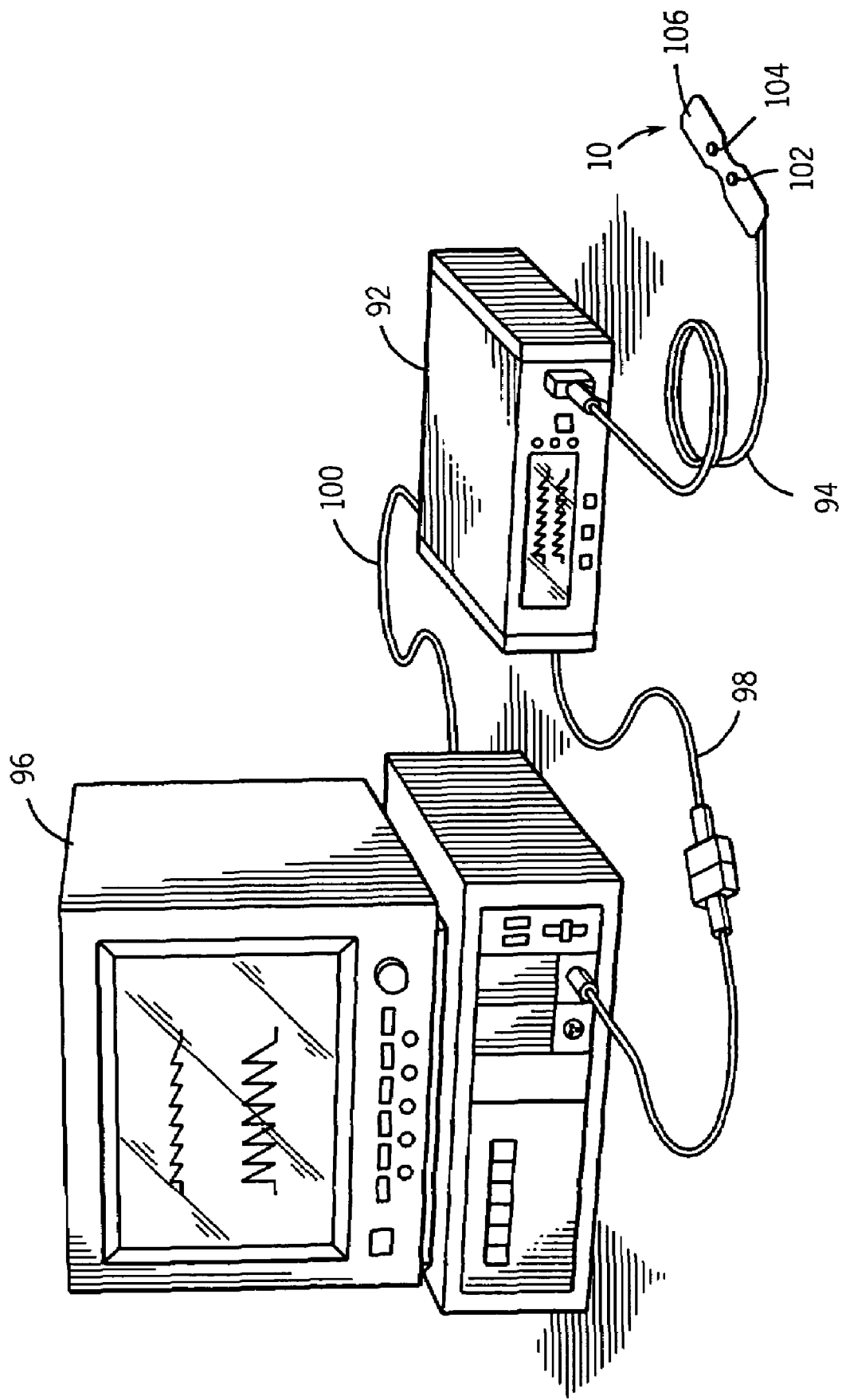
FIG. 10 illustrates a pulse oximetry system coupled to a multi-parameter patient monitor and a sensor according to embodiments of the present invention.

A sensor, illustrated generically as a sensor 10, may be used in conjunction with a pulse oximetry monitor 92, as illustrated in FIG. 10. It should be appreciated that the cable 94 of the sensor 10 may be coupled to the monitor 92 or it may be coupled to a transmission device (not shown) to facilitate wireless transmission between the sensor 10 and the monitor 92. The monitor 92 may be any suitable pulse oximeter, such as those available from Nellcor Puritan Bennett Inc. Furthermore, to upgrade conventional pulse oximetry provided by the monitor 92 to provide additional functions, the monitor 92 may be coupled to a multi-parameter patient monitor 96 via a cable 98 connected to a sensor input port or via a cable 100 connected to a digital communication port.

The sensor 10 includes an emitter 102 and a detector 104 that may be of any suitable type. For example, the emitter 102 may be one or more light emitting diodes adapted to transmit one or more wavelengths of light in the red to infrared range, and the detector 104 may one or more photodetectors selected to receive light in the range or ranges emitted from the emitter 102. Alternatively, an emitter may also be a laser diode or a vertical cavity surface emitting laser (VCSEL). An emitter and detector may also include optical fiber sensing elements. An emitter may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 102 and the detector 104 may be disposed on a sensor body 106, which may be made of any suitable material, such as plastic, foam, woven material, or paper, and may include elastic portions. Alternatively, the emitter 102 and the detector 104 may be remotely located and optically coupled to the sensor 10 using optical fibers. In the depicted embodiments, the sensor 10 is coupled to a cable 94 that is responsible for transmitting electrical and/or optical signals to and from the emitter 102 and detector 104 of the sensor 10. The cable 94 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 102 and detector 104 that are typically placed on opposing sides of the sensor site. If the sensor site is a fingertip, for example, the sensor 10 is positioned over the patient's fingertip such that the emitter 102 and detector 104 lie on either side of the patient's nail bed. In other words, the sensor 10 is positioned so that the emitter 102 is located on the patient's fingernail and the detector 104 is located 180° opposite the emitter 102 on the patient's finger pad. During operation, the emitter 102 shines one or more wavelengths of light through the patient's fingertip and the light received by the detector 104 is processed to determine various physiological characteristics of the patient. In each of the embodiments discussed herein, it should be understood that the locations of the emitter 102 and the detector 104 may be exchanged. For example, the detector 104 may be located at the top of the finger and the emitter 102 may be located underneath the finger. In either arrangement, the sensor 10 will perform in substantially the same manner.

Reflectance type sensors also operate by emitting light into the tissue and detecting the light that is transmitted and scattered by the tissue. However, reflectance type sensors include an emitter 102 and detector 104 that are typically placed on the same side of the sensor site. For example, a reflectance type sensor may be placed on a patient's finger or forehead such that the emitter 102 and detector 104 lie side-by-side. Reflectance type sensors detect light photons that are scattered back to the detector 152. A sensor 10 may also be a "transflectance" sensor, such as a sensor that may subtend a portion of a patient's heel.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood and/or tissue constituents using principles of pulse oximetry. For example, using the same, different, or additional wavelengths, the present techniques may be utilized for the measurement and/or analysis of carboxyhemoglobin, methemoglobin, total hemoglobin, fractional hemoglobin, intravascular dyes, hematocrit, carbon dioxide, carbon monoxide, protein, lipid and/or water content or compartmentalization. Rather, the invention is to cover all modifications, equivalents, and alternatives falling within the spirit and scope of the invention as defined by the following appended claims.

What is claimed is:

1. A sensor comprising:
an emitter and a detector coupled to a substantially rigid substrate, the substrate being disposed on a tissue-contacting surface of a bandage-type sensor body configured to extend over a digit, wherein the substantially rigid substrate is adapted to hold the emitter and detector at a substantially fixed optical distance relative to one another when the sensor is applied to a patient, and wherein the bandage-type sensor body comprises sufficient elastic material to accommodate digit movement within the sensor.

2. The sensor, as set forth in claim 1, wherein the sensor comprises at least one of a pulse oximetry sensor or a sensor for measuring a water fraction.

3. The sensor, as set forth in claim 1, wherein the emitter comprises at least one light emitting diode.

4. The sensor, as set forth in claim 1, wherein the detector comprises at least one photodetector.

5. The sensor, as set forth in claim 1, wherein the emitter and the detector are embedded within the substantially rigid substrate.

6. The sensor, as set forth in claim 1, wherein the substantially rigid substrate comprises a metal or a rigid polymeric material.

7. The sensor, as set forth in claim 1, wherein the emitter and the detector are operatively coupled to a sensor cable.

8. A pulse oximetry system comprising:
a pulse oximetry monitor; and
a pulse oximetry sensor adapted to be operatively coupled to the monitor, the sensor comprising:
an emitter and a detector coupled to a substantially rigid substrate, the substrate being disposed on a tissue-contacting surface of a bandage-type sensor body configured to extend over a digit, wherein the substantially rigid substrate is adapted to hold the emitter and detector at a substantially fixed optical distance relative to one another when the sensor is applied to a patient, and wherein the bandage-type sensor body comprises sufficient elastic material to accommodate digit movement within the sensor.

9. The system, as set forth in claim 8, wherein the sensor comprises at least one of a pulse oximetry sensor or a sensor for measuring a water fraction.

10. The system, as set forth in claim 8, wherein the emitter comprises at least one light emitting diode.

11. The system, as set forth in claim 8, wherein the detector comprises at least one photodetector.

12. The system, as set forth in claim 8, wherein the emitter and the detector are embedded within the substantially rigid substrate.

13. The system, as set forth in claim 8, wherein the substantially rigid substrate comprises a metal or a rigid polymeric material.

14. The system, as set forth in claim 9, wherein the emitter and the detector are operatively coupled to a sensor cable.

15. A method comprising:
fixing the optical distance between an emitter and a detector relative to one another, wherein the emitter and the detector are disposed on a substantially rigid substrate, the substrate being disposed on a tissue-contacting surface of a bandage-type sensor body configured to extend over a digit, wherein the bandage-type sensor body comprises sufficient elastic material to accommodate digit movement within the sensor.

16. The method, as set forth in claim 15, wherein fixing the optical distance between the emitter and the detector comprises embedding the emitter and the detector in the substantially rigid substrate.

17. A method of manufacturing a pulse oximetry sensor, comprising:
providing a substantially rigid substrate, the substrate being disposed on a tissue-contacting surface of a bandage-type sensor body configured to extend over a digit to which an emitter and a detector are coupled, wherein the substantially rigid substrate is adapted to hold the emitter and the detector at a substantially fixed optical distance, and wherein the bandage-type sensor body comprises sufficient elastic material to accommodate digit movement within the sensor.

18. The method, as set forth in claim 17, comprising:
embedding the emitter and the detector within the substantially rigid substrate.

19. The method, as set forth in claim 17, wherein the substantially rigid substrate comprises a metal or a rigid polymeric material.

20. The method, as set forth in claim 17, wherein the emitter and the detector are operatively coupled to a sensor cable.

* * * * *